United States Patent
Saukkonen et al.

(10) Patent No.: US 11,795,280 B2
(45) Date of Patent: Oct. 24, 2023

(54) METHOD FOR PRODUCING A FILM HAVING GOOD BARRIER PROPERTIES AND A FILM HAVING GOOD BARRIER PROPERTIES

(71) Applicant: Stora Enso OYJ, Helsinki (FI)

(72) Inventors: Esa Saukkonen, Lappeenranta (FI); Isto Heiskanen, Imatra (FI); Kaj Backfolk, Lappeenranta (FI); Katja Lyytikäinen, Imatra (FI)

(73) Assignee: Stora Enso OYJ, Helsinki (FI)

( * ) Notice: Subject to any disclaimer, the term of this patent is extended or adjusted under 35 U.S.C. 154(b) by 574 days.

(21) Appl. No.: 16/757,093

(22) PCT Filed: Oct. 17, 2018

(86) PCT No.: PCT/IB2018/058043
§ 371 (c)(1),
(2) Date: Apr. 17, 2020

(87) PCT Pub. No.: WO2019/077514
PCT Pub. Date: Apr. 25, 2019

(65) Prior Publication Data
US 2020/0239652 A1    Jul. 30, 2020

(30) Foreign Application Priority Data
Oct. 20, 2017    (SE) .................... 1751305-2

(51) Int. Cl.
| C08J 5/18 | (2006.01) |
| C12N 9/42 | (2006.01) |
| C12N 9/24 | (2006.01) |
| D21H 11/18 | (2006.01) |
| D21H 11/20 | (2006.01) |
| D21H 17/00 | (2006.01) |
| D21H 17/05 | (2006.01) |
| D21H 19/34 | (2006.01) |
| D21H 19/52 | (2006.01) |

(52) U.S. Cl.
CPC ............... *C08J 5/18* (2013.01); *C12N 9/248* (2013.01); *C12N 9/2437* (2013.01); *D21H 11/18* (2013.01); *D21H 11/20* (2013.01); *D21H 17/005* (2013.01); *D21H 17/05* (2013.01); *D21H 19/34* (2013.01); *D21H 19/52* (2013.01)

(58) Field of Classification Search
CPC ...... D21H 11/18; D21H 11/20; D21H 17/005; D21H 17/05; D21H 19/34; D21H 19/52; C12N 9/2437; C12N 9/248; C12N 9/2488; C08J 5/18; C08J 9/24
See application file for complete search history.

(56) References Cited

U.S. PATENT DOCUMENTS

| 6,613,528 B2 * | 9/2003 | Helbert ..................... C12Q 1/34 435/6.16 |
| 10,676,868 B2 * | 6/2020 | Heiskanen ............... B29D 7/01 |
| 10,774,472 B2 * | 9/2020 | Sebastian ............... D21H 11/18 |
| 10,865,280 B2 * | 12/2020 | Kunnari ................. D21H 11/18 |
| 11,124,920 B2 * | 9/2021 | Salas Araujo ......... D21H 11/18 |
| 11,248,343 B2 * | 2/2022 | Knöös ....................... C08L 1/02 |
| 11,377,791 B2 * | 7/2022 | Husband .............. D21H 19/385 |
| 11,512,020 B2 * | 11/2022 | Skuse ................... C04B 24/383 |
| 2007/0163735 A1 | 7/2007 | Buchert et al. |
| 2012/0216718 A1 | 8/2012 | Berglund et al. |
| 2013/0047893 A1 | 2/2013 | Heiskanen et al. |
| 2015/0167243 A1 | 6/2015 | Bilodeau et al. |
| 2019/0002658 A1 * | 1/2019 | Kunnari ................. D21H 11/20 |
| 2020/0239652 A1 * | 7/2020 | Saukkonen .......... C12N 9/2437 |
| 2021/0207324 A1 * | 7/2021 | Knöös ....................... C08L 1/02 |
| 2021/0372054 A1 * | 12/2021 | Salas Araujo .......... D21F 5/181 |
| 2022/0185975 A1 * | 6/2022 | Kumar ................. B29C 43/003 |

FOREIGN PATENT DOCUMENTS

| CA | 3002729 C | * | 12/2020 | ............... C08J 5/18 |
| CN | 106480129 A | | 3/2017 | |
| EP | 2548918 A1 | | 1/2013 | |
| EP | 2516156 B1 | * | 3/2019 | .......... B32B 15/085 |
| EP | 3350372 B1 | * | 1/2020 | ............... C08J 5/18 |
| EP | 3350371 B1 | * | 2/2020 | ............ D21H 11/18 |
| JP | 2007515570 A | | 6/2007 | |
| JP | 2009298972 A | | 12/2009 | |
| JP | 2010202987 A | | 9/2010 | |
| JP | 2013510963 A | | 3/2013 | |
| JP | 2013110987 A | | 6/2013 | |
| SE | 539629 C2 | * | 10/2017 | ............... C08J 5/18 |
| WO | WO-0125470 A1 | * | 4/2001 | ............... C08J 5/18 |
| WO | 2011004301 A1 | | 1/2011 | |
| WO | 2011162160 A1 | | 12/2011 | |
| WO | 2012043103 A1 | | 5/2012 | |
| WO | 2014181560 A1 | | 11/2014 | |
| WO | 2017046751 A1 | | 3/2017 | |
| WO | 2017046755 A1 | | 3/2017 | |
| WO | WO-2017046749 A1 | * | 3/2017 | ............... C08J 5/18 |
| WO | 2017168353 A1 | | 10/2017 | |
| WO | WO-2019077514 A1 | * | 4/2019 | ............... C08J 5/18 |
| WO | WO-2021053428 A1 | * | 3/2021 | ............. D21F 11/14 |
| WO | WO-2022189957 A1 | * | 9/2022 | |
| WO | WO-2022189958 A1 | * | 9/2022 | |

OTHER PUBLICATIONS

Wang, Wangxia et al., Endoglucanase post-milling treatment for producing cellulose nanofibers from bleached eucalyptus fibers by a supermasscolloider, Cellulose (2016) 23: 1859-1870.
Kristensen, Jan B. et al., Yield-determining factors in high-solids enzymatic hydrolysis of lignocellulose, Biotechnology for Biofuels 2009, 2:11, Jun. 2009.

* cited by examiner

*Primary Examiner* — Jose A Fortuna
(74) *Attorney, Agent, or Firm* — Greer, Burns & Crain, Ltd.

(57) ABSTRACT

The present invention relates to a method for manufacturing a film comprising microfibrillated cellulose wherein the method comprises the steps of; providing a suspension comprising a microfibrillated cellulose, adding an enzyme to the suspension, mixing the enzyme with the suspension to form a mixture, applying said mixture to a wire to form a fibrous web and drying said web to form said film. The present invention further relates to a film comprising microfibrillated cellulose having good barrier properties.

20 Claims, No Drawings

METHOD FOR PRODUCING A FILM HAVING GOOD BARRIER PROPERTIES AND A FILM HAVING GOOD BARRIER PROPERTIES

This application is a U.S. National Phase under 35 U.S.C. § 371 of International Application No. PCT/IB2018/058043, filed Oct. 17, 2018, which claims priority under 35 U.S.C. §§ 119 and 365 to Swedish Application No. 1751305-2, filed Oct. 20, 2017.

TECHNICAL FIELD

The present invention relates to a barrier film having a good and stable oxygen transmission rate (OTR) even at high relative humidity's (RH). More particularly, the present invention relates to a method of manufacturing such a film and a film produced.

BACKGROUND

Today, films comprising microfibrillated cellulose (MFC), have proven to give excellent barrier properties (see e.g. Aulin et al., Oxygen and oil barrier properties of microfibrillated cellulose films and coatings, Cellulose (2010) 17:559-574, Lavoine et al., Microfibrillated cellulose—Its barrier properties and applications in cellulosic materials: A review, Carbohydrate polymers 90 (2012) 735-764, Kumar et al., Comparison of nano- and microfibrillated cellulose films, Cellulose (2014) 21:3443-3456), whereas the gas barrier properties are very dependent on the moisture or the relative humidity in the surrounding environment. Therefore, it is quite common that MFC films have to be coated with a polymer film to prevent moisture or water vapor to swell and disrupt the MFC film.

The lack of gas barrier properties such as oxygen or air, at high relative humidity has been investigated and described but most of the suggested solutions are expensive and difficult to implement in industrial scale. One route is to modify the MFC or nanocellulose such as disclosed in EP2554589A1 where MFC dispersion was modified with silane coupling agent. The EP2551104A1 teaches the use of MFC and polyvinyl alcohol (PVOH) and/or polyuronic acid with improved barrier properties at higher relative humidity (RH). Another solution is to coat the film with a film having good barrier properties at high RH and/or low water vapor transmission rate. The JP2000303386A discloses e.g. latex coated on MFC film, while US2012094047A teaches the use of wood hydrolysates mixed with polysaccharides such as MFC that can be coated with a polyolefin layer. In addition to this chemical modification, the possibility of cross-linking fibrils or fibrils and copolymers has been investigated. This improves water fastness of the films but also water vapor transmission rates. EP2371892A1, EP2371893A1, claims cross-linking MFC with metal ions, glyoxal, glutaraldehyde and/or citric acid, respectively.

There are also challenges with production of a MFC film with good barrier properties. It is especially challenge to dewater the film at high production speeds due to the characteristics properties of microfibrillated cellulose. When MFC films are used as barriers, it is crucial that the films don't have any pinholes or other defects that negatively would affect the barrier properties. Thus, it is important that the surface of the MFC film is smooth making the dewatering even more challenging since wire markings or other surface defects will negatively affect the barrier properties of the film.

There is thus a need to find a simple solution for producing films having good barrier properties even at high humidity and at high production speed.

SUMMARY

It is an object of the present invention, to provide a film comprising microfibrillated cellulose, which has improved barrier properties even at higher relative humidity in the surroundings.

It is an object of the present invention to provide a film comprising microfibrillated cellulose that can be produced at higher production speeds.

The invention is defined by the appended independent claims. Embodiments are set forth in the appended dependent claims and in the following description and drawings.

The present invention relates to a method for manufacturing a film wherein the method comprises the steps of; providing a suspension comprising a microfibrillated cellulose, adding an enzyme to the suspension, mixing the enzyme with the suspension to form a mixture, applying said mixture to a wire to form a fibrous web and drying said web to form said film. With the addition of an enzyme to the suspension comprising microfibrillated cellulose it was surprisingly found that the dewatering of the formed fibrous web was improved. Even more surprising was that the barrier properties of the formed film was remained or even improved, even at high humidity.

The enzyme is preferably an enzyme decomposing cellulose and/or hemicellulose such as cellulase, xylanase and/or mannanase.

The enzyme may be cellulase with an activity above 20 0000 CMU/g and/or xylanase with an activity above 20 0000 nkat/ml.

The microfibrillated cellulose is preferably native, i.e. it is a chemically unmodified microfibrillated cellulose.

The temperature of the suspension when the enzyme is added is preferably between 30-70° C. By increasing the temperature of the suspension the microfibrillated cellulose material is more accessible for the enzyme.

The mixture is preferably stored for a period of at least 5 minutes, preferably at least 15 minutes or even more preferably at least 30 minutes before being applied to said wire. The storage time needs to be sufficient in order to make sure that the enzyme has enough time to decompose the material needed.

The dry content of the mixture is preferably between 0.01-0.5% by weight. The dry content before addition of the enzymes needs to low enough so the enzymes can be evenly mixed in the suspension.

The method may further comprise the step of mechanical treating the suspension comprising microfibrillated cellulose prior to the addition of the enzyme. In this way the MFC will be more reactive to the enzymatic treatment.

The wire is preferably part of a paper or board machine making it possible to produce the film at high production speeds.

The fibrous web is preferably dewatered on the wire. The dewatering rate on the wire is improved with the present invention.

The production speed on the wire is preferably between 150-1500 m/min. It has been found possible to be able to produce a film comprising MFC and even very high amounts of MFC at a high production speed.

The dry content of the fibrous web before drying is preferably between 20-50% by weight. By the present invention it is possible to increase the dry content before drying due to the improved dewatering properties of the MFC used. Thus, the demand of the subsequent drying step is reduced and the drying can then be done at a lower energy demand or at shorter time.

The drying is preferably done at a temperature between 100-150° C. During drying it is important that the barrier properties of the film is not destroyed.

The mixture may further comprise any one of a starch, carboxymethyl cellulose, a filler, retention chemicals, flocculation additives, deflocculating additives, dry strength additives, wet strength additives, softeners, surface active agents or mixtures thereof. It may be possible to add additives that will improve different properties of the mixture and/or the produced film. It has been found that the retention of chemicals in the web or film is improved. Therefore, the amount of chemicals can be reduced without reducing their effects.

The film preferably has an oxygen transmission rate in the range of from 0.1 to 300 $cc/m^2/24$ h according to ASTM D-3985, at a relative humidity of 50% at 23° C. and/or at a relative humidity of 85% at 38° C.

The suspension preferably comprises between 50-100 wt-% of microfibrillated cellulose by total amount of organic material in the suspension.

The present invention further relates to a film produced according to the method described above wherein said film comprises microfibrillated cellulose and has an oxygen transmission rate in the range of from 0.1 to 300 $cc/m^2/24$ h measured according to ASTM D-3985, at a relative humidity of 50% at 23° C. and/or at a relative humidity of 85% at 38° C. By the present invention it is possible to produce a film that has very good oxygen barrier properties at high humidity.

The film preferably has a basis weight of less than 100 $g/m^2$, preferably between 10-100 $g/m^2$. Since the dewatering properties of the film is improved it is possible to produce a film with higher basis weight at good production speed.

The film is preferably a multilayer film comprising more than one layer.

The film preferably comprises between 50-100 wt-% of microfibrillated cellulose by total amount of organic material of the film.

DETAILED DESCRIPTION

The method according to the present invention relates to a method for manufacturing a film wherein the method comprises the steps of: providing a suspension comprising a microfibrillated cellulose, adding an enzyme to the suspension, mixing the enzyme with the suspension to form a mixture, applying said mixture to a wire to form a fibrous web and drying said web to form said film. With the addition of an enzyme to the suspension comprising microfibrillated cellulose it was surprisingly found that the dewatering of the formed fibrous web was improved. Even more surprising was that the barrier properties of the formed film was remained or even improved, even at high humidity. The oxygen barrier properties of the film was shown to improve. Also, the grease and aroma barrier properties of the film was improved. By addition of a cellulose decomposing enzyme to the suspension comprising microfibrillated cellulose the enzyme will decompose or "eat" the microfibrillated cellulose. The enzyme will attach to accessible surface areas of the fibrils and decompose it to even smaller fibrils or dissolve it by decomposing the MFC to mono- oligo- or polysaccharides. It was found that the smallest MFC materials have the largest number of accessible surface areas, leading to that the enzymes attaches and decomposes the finer material to a larger extent compared to the coarser MFC material present. During dewatering of the fibrous web the decomposed or dissolved fine material will be removed, i.e. the retention of the finest material is reduced, leading to that the dewatering of the produced MFC film is strongly improved. Due to the removal of the finer material the barrier properties of the film were expected to be deteriorated. Surprisingly, it was the other way around. The barrier properties were shown to be improved. Apparently, the addition of the enzyme also resulted in a narrower fibril size distribution meaning that more of the finest material is removed as discussed above but also that the coarsest material are decomposed forming a finer material. The largest or most coarse fibrils will give the film improved strength but too much coarse material will strongly decrease the barrier properties of the film.

Even more surprisingly was that the barrier properties at high humidity of the film were improved. Apparently, the enzymatic treatment of the MFC material will affect the moisture absorption properties of the film. The enzyme will decompose the MFC material in such a way that the moisture absorption properties of the material is reduced leading to that the MFC film will be more resistant against high humidity.

Another theory to the improved barrier and dewatering properties of the film is that the retention of additives added to the mixture is improved. Thus, the presence of e.g. retention chemicals or strength chemicals is increased which also leads to improved dewatering and improved physical properties of the film. Thus, another advantage with the present invention is that the amount of chemicals added can be reduced since the retention of the chemicals is improved.

The enzyme added to the suspension is preferably an enzyme that decomposes cellulose and/or hemicellulose, such as cellulase, xylanase and/or mannanse. Depending on the type of the microfibrillated cellulose it is possible to tailor made the enzymatic composition to either comprise only one kind of enzyme or to use mixture of different enzymes. The enzyme may be cellulase with an activity above 20 0000 CMU/g which activity may be determined on a CMC substrate at 60° C. and pH 4.8. The enzyme may also be xylanase with an activity above 20 0000 nkat/ml when measured against birch xylan at pH 5, 50° C. and a 50 mM Na-citrate as pH buffer. It may be preferred to use a mixture of both cellulase and xylanase.

The microfibrillated cellulose is preferably native, i.e. it is a chemically unmodified microfibrillated cellulose. Native microfibrillated cellulose comprises both cellulose and hemicellulose and a mixture of cellulase and xylanase may then be preferred to use.

The temperature of the suspension comprising MFC is preferably between 30-70° C., even more preferably between 40-60° C., before the enzyme is added to the suspension. By increasing the temperature of the suspension, the microfibrillated cellulose material in the suspension is more accessible for the enzyme. It is thus possible to add less enzymes or to decrease the storage time for the mixture. The temperature range chosen is dependent on the enzyme used and on the optimal working conditions for that specific enzyme or mixture of enzymes.

The pH value of the suspension comprising MFC is preferably between 4-8, even more preferably between 5-7, before the enzyme is added to the suspension. It is important that the pH value of the suspension is within the mentioned range so the climate for the enzyme is as beneficial as possible. Too high or too low pH will either decrease the activity of the enzyme or even deactivate it.

The enzyme is added to the suspension in any suitable way. If the production of the film is done on a paper or paperboard machine it is possible to add the enzyme to the white water being recovered from the dewatering of the mixture on the wire. The white water comprising the enzyme is thereafter added to the suspension. The enzyme may also be added during production of the MFC, preferably to the last mechanical treatment stage of the fibers to produce MFC. However, it is important that the addition of the enzymes is not done too soon if added during MFC production. It is important that the suspension comprises a substantially amount of MFC in order for the treatment with enzymes to efficient.

The suspension and the enzyme is mixed to form a mixture and it is important that the mixing is thorough making the enzyme to be in contact with all the fines and fibrils in the suspension. The mixing may be done in any conventional way. It might for example be possible to mix the enzyme with the suspension by using a high shear mixing device or by pumping the suspension and the enzyme.

After the enzyme and suspension is mixed the mixture need to be stored for a certain period of time to make sure that the enzyme has enough time to decompose the material. It is preferred that the mixture is stored for a period of at least 5 minutes, preferably at least 15 minutes or even more preferably at least 30 minutes before being applied to said wire.

By measuring for example the viscosity, the water retention value, the amount of sugars or by measuring the dewatering rate of the mixture it is possible to determine when the enzymatic treatment is sufficient, i.e. how long time is needed, which enzyme to use, how much enzyme to dose and which activity of the enzyme that is needed. Parameters that can affect the enzymatic activity and which needs to be optimized are e.g. time, temperature, pH value of the mixture and the amount and activity of the enzyme. The present invention improves the dewatering of a suspension comprising microfibrillated cellulose and it is well known for a person skilled in the art to know when a good or adequate dewatering is achieved. Thus, it is obvious for a person skilled in the art to optimize the enzymatic treatment so that good dewatering properties of the suspension comprising microfibrillated cellulose is achieved.

It is possible that the suspension is a suspension which is a fraction of a first suspension. The method according to the invention may then comprise the steps of: providing a first suspension comprising microfibrillated cellulose, fractionate the first suspension into a suspension and a second suspension, adding enzyme to the suspension, mixing the enzyme with the suspension to form a mixture, optionally mixing the mixture with the second suspension to form a second mixture, applying said mixture or optional second mixture to a wire to form a fibrous web and drying said web to form said film.

The second suspension may also be treated with enzymes before being mixed with the mixture. The fraction of the second suspension is preferably the reject, i.e. comprising a larger MFC material. One advantage with fractionating the first suspension is that the enzymatic treatment can be more tailor made since the material of each fraction will be homogenous and the optimal enzymatic treatment can then easier be applied.

The method may further comprise the step of mechanical treating the suspension comprising microfibrillated cellulose prior to the addition of the enzyme. In this way, the active surfaces of the microfibrillated cellulose is increased making the MFC more reactive to the enzymatic treatment. The mechanical treatment may be done in any conventional way, e.g. by refining or homogenization.

The film is thereafter produced by applying said mixture or second mixture to a wire to form a fibrous web and drying said web to form at least one layer of said film. The dry content of the at least one layer of the film after drying is preferably above 95% by weight.

The drying is preferably done by increasing the temperatures. Temperatures used during drying may be between 50-200° C., preferably between 100-150° C. The drying may be done in any conventional equipment. During drying the enzymes is killed leaving no residual enzyme activity in the final product, which is important if the film should be used in e.g. food contact applications. Thus, it is important that the temperature during drying is high enough to kill the enzymes. Also, since the dry content of the film is increased, preferably to above 95% by weight, the activity of the enzymes is terminated at such high dry contents. It is also possible to kill the enzymes by other methods than applying heat, e.g. by radiation or addition of chemicals. It is important that the produced film has no residual enzyme activity if to be used for sensitive end uses e.g. in food applications.

The wire is preferably a wire of a paper making machine, i.e. any kind of paper making machine known to a person skilled in the art used for making paper, paperboard, tissue or any similar products. The mixture is the applied onto the wire and the fibrous web formed on the wire is then dewatered. The dewatered fibrous web is thereafter dried by increasing the temperature of the web to form the film.

It may also be possible that the mixture is applied onto a fibrous web on a wire, to produce a paper or paperboard product to which the mixture is applied to form a coated product.

The production speed for the production of the film on a wire is preferably between 150-1500 m/min, preferably between 200-1200 m/min and even more preferred between 300-1000 m/min. It has been found possible to be able to produce a MFC film having good barrier properties at an increased production speed due to the improved dewatering properties of the MFC used.

The microfibrillated cellulose of the suspension is produced from mechanical, thermomechanical or chemical pulp. The microfibrillated cellulose is preferably produced from kraft pulp. The microfibrillated cellulose preferably has a Schopper Riegler value (SR°) of more than 80, preferably more than 90, even more preferred more than 93 or even more preferred more than 95. The Schopper-Riegler value can be obtained through the standard method defined in EN ISO 5267-1. This high SR value is determined for a pulp, with or without additional chemicals, thus the fibers have not consolidated into a film or started e.g. hornification. The dry solid content of this kind of web, before disintegrated and measuring SR, is less than 50% (w/w). To determine the Schopper Riegler value it is preferable to take a sample just after the wire section or from the headbox where the wet web consistency is relatively low. The skilled person understands that paper making chemicals, such as retention agents or dewatering agents, have an impact on the SR value. The SR value specified herein, is to be understood as an indication but not a limitation, to reflect the characteristics of the MFC material itself. The microfibrillated cellulose is preferably produced from never dried pulp since it was found that never dried MFC has much higher accessibility for enzymes compared to MFC produced from dried pulp. It is also preferred that the microfibrillated cellulose has a very low lignin content since lignin could negatively affect the enzymatic activity.

The mixture may further comprise additives, preferably any one of a starch, carboxymethyl cellulose, a filler, retention chemicals, flocculation additives, deflocculating additives, dry strength additives, wet strength additives, softeners, surface active agents, or mixtures thereof. It may be possible to add additives that will improve different properties of the mixture and/or the produced film.

The present invention also relates to a film, comprising microfibrillated cellulose, which film has an oxygen transmission rate in the range of from 0.1 to 300 cc/m$^2$/24 h measured according to the standard ASTM D-3985, at a relative humidity of 50% at 23° C. and/or at a relative humidity of 85% at 38° C.

The amount of microfibrillated cellulose in the produced film and thus also in the suspension is preferably between 50-100 wt-% by total dry weight of the film, preferably between 60-100 wt-% by total dry weight of the film and even more preferred between 70-100% by total dry weight of the film. Thus, the film or suspension may also comprises longer or normal cellulosic fibers as well, preferably chemical, mechanical or thermomechanical pulp fibers. The fibers may be produced from hardwood or softwood fibers.

According to one embodiment the film may have a basis weight of less than 100 g/m$^2$, or less than 70 g/m$^2$, or less than 50 g/m$^2$, or less than 40 g/m$^2$, or less than 30 g/m$^2$. The basis weight is preferably at least 10 g/m$^2$, preferably between 10-100 g/m$^2$, even more preferred between 10-70 g/m$^2$, more preferred between 10-50 g/m$^2$ and most preferred between 10-30 g/m$^2$.

Microfibrillated cellulose (MFC) shall in the context of the patent application mean a nano scale cellulose particle fiber or fibril with at least one dimension less than 100 nm. MFC comprises partly or totally fibrillated cellulose or lignocellulose fibers. The liberated fibrils have a diameter less than 100 nm, whereas the actual fibril diameter or particle size distribution and/or aspect ratio (length/width) depends on the source and the manufacturing methods. The smallest fibril is called elementary fibril and has a diameter of approximately 2-4 nm (see e.g. Chinga-Carrasco, G., *Cellulose fibres, nanofibrils and microfibrils: The morphological sequence of MFC components from a plant physiology and fibre technology point of view, Nanoscale research letters* 2011, 6:417), while it is common that the aggregated form of the elementary fibrils, also defined as microfibril (Fengel, D., *Ultrastructural behavior of cell wall polysaccharides, Tappi J.*, March 1970, Vol 53, No. 3.), is the main product that is obtained when making MFC e.g. by using an extended refining process or pressure-drop disintegration process. Depending on the source and the manufacturing process, the length of the fibrils can vary from around 1 to more than 10 micrometers. A coarse MFC grade might contain a substantial fraction of fibrillated fibers, i.e. protruding fibrils from the tracheid (cellulose fiber), and with a certain amount of fibrils liberated from the tracheid (cellulose fiber).

There are different acronyms for MFC such as cellulose microfibrils, fibrillated cellulose, nanofibrillated cellulose, fibril aggregates, nanoscale cellulose fibrils, cellulose nanofibers, cellulose nanofibrils, cellulose microfibers, cellulose fibrils, microfibrillar cellulose, microfibril aggregrates and cellulose microfibril aggregates. MFC can also be characterized by various physical or physical-chemical properties such as large surface area or its ability to form a gel-like material at low solids (1-5 wt %) when dispersed in water.

The cellulose fiber is preferably fibrillated to such an extent that the final specific surface area of the formed MFC is from about 1 to about 200 m2/g, or more preferably 50-200 m2/g when determined for a freeze-dried material with the BET method.

Various methods exist to make MFC, such as single or multiple pass refining, pre-hydrolysis followed by refining or high shear disintegration or liberation of fibrils. One or several pre-treatment step is usually required in order to make MFC manufacturing both energy efficient and sustainable. The cellulose fibers of the pulp to be supplied may thus be pre-treated enzymatically or chemically, for example to hydrolyse or swell fiber or reduce the quantity of hemicellulose or lignin.

The nanofibrillar cellulose may contain some hemicelluloses; the amount is dependent on the plant source. Mechanical disintegration of the pre-treated fibersis carried out with suitable equipment such as a refiner, grinder, homogenizer, colloider, friction grinder, ultrasound sonicator, fluidizer such as microfluidizer, macrofluidizer or fluidizer-type homogenizer. Depending on the MFC manufacturing method, the product might also contain fines, or nanocrystalline cellulose or e.g. other chemicals present in wood fibers or in papermaking process. The product might also contain various amounts of micron size fiber particles that have not been efficiently fibrillated. MFC is produced from wood cellulose fibers, both from hardwood or softwood fibers. It can also be made from microbial sources, agricultural fibers such as wheat straw pulp, bamboo, bagasse, or other non-wood fiber sources. It is preferably made from pulp including pulp from virgin fiber, e.g. mechanical, chemical and/or thermomechanical pulps. It can also be made from broke or recycled paper.

The above described definition of MFC includes, but is not limited to, the new proposed TAPPI standard W13021 on cellulose nanofibril (CNF) defining a cellulose nanofiber material containing multiple elementary fibrils with both crystalline and amorphous regions, having a high aspect ratio with width of 5-30 nm and aspect ratio usually greater than 50.

EXAMPLES

Example 1

Trials were conducted on a pilot paper machine to produce a MFC film. In addition to a microfibrillated (MFC) suspension, a retention system comprising wet-end starch, cationic polysaccharide, retention chemical and wet-strength chemical were used, (reference test point KP4.1). In addition, enzymes in the form of cellulase 5 kg/t or xylanase 10 kg/t were dosed to the paper machine circulation waters in KP5 and KP6, respectively.

The addition of enzymes improved the dewatering on the wire section, which was noticed as the water line on the Fourdnier wire was closer to the headbox. The first value of the water line in the table below represents at which suction box the line appears. Lower number is closer to the headbox meaning that dewatering is improved. Furthermore, each suction box has been divided into five different areas. The second number represents which area of respectively suction box the water line appears to give an even more precise value.

The activity of the enzyme used in KP5 was 96 400 CMU/g and the activity of the enzyme used in KP6 was 63 300 nkat/ml.

The test points having enzyme dosing (KP5 and KP6) in the wet-end had improved oxygen barrier properties compared to reference test point KP 4.1 showing as the oxygen transmission rate (OTR) was substantially lower with the test points KP5 and KP6. Furthermore, the dewatering rate of the films according to the invention (KP5 and KP6) was improved.

TABLE 1

Test points and measured OTR value and dewatering

|  | KP 4.1 | KP5 | KP6 |
|---|---|---|---|
| Fiber source, % | MFC 100 | MFC 100 | MFC 100 |
| Enzyme | — | Cellulase 5 kg/t | Xylanase HC 10 kg/t |
| Water line | 3/0 | 2/3 | 2/3 |
| Grammage, g/m$^2$ | 31.3 | 31.8 | 30.9 |
| OTR 23° C./50% RH, cc/m2*day | 707 | 11 | 12 |

Example 2

The MFC films KP 4.1, KP5 and KP6 produced in the same was as in Example 1 were extrusion polyethylene-coated with 25 g/m$^2$ of low-density polyethylene (LDPE).

The oxygen transmission rate (OTR) of the PE-coated MFC films was measured in 38° C. and 85% relative humidity (RH) conditions, i.e. tropical conditions. Also, the OTR was measured after storing the PE-coated films in 38° C. and 85% RH for 3 weeks.

The results in Table 2 show that the oxygen transmission rate (OTR) in tropical conditions were lower for the films KP5 and KP6, both before and after conditioning the films in 38° C. and 85% RH for 3 weeks. Thus, the oxygen barrier properties of the films according to the invention were improved.

TABLE 2

Results for the PE-coated test points

|  | KP 4.1 | KP5 | KP6 |
|---|---|---|---|
| OTR 38° C./85% RH, cc/m2*day | 77 | 69 | 56 |
| OTR 23° C./50% RH, cc/m2*day, after 3 weeks storage | 86 | 81 | 78 |

Example 3

The oil and grease resistance of the MFC films KP 4.1, KP5 and KP6 were tested according to the modified ASTM F119-82 method. Chicken fat was used as grease and the test was performed in an oven at 60° C.

The results from the test are presented in Table 3. It can be seen from the results that the oil and grease resistance of the MFC films is slightly improved when enzymes were dosed to paper machine circulation waters (KP5 and KP6). Consequently, the film produced according to the present invention also have good grease barrier properties.

TABLE 3

Results from oil and grease resistance testing

| | | | 0-15 min | -30 min | -45 min | -1 hour | -2 hours | -3 hours | -4 hours | -5 hours | -6 hours | -7 hours | -8 hours | -24 hours | -28 hours |
|---|---|---|---|---|---|---|---|---|---|---|---|---|---|---|---|
| KP 4.1 | Flat | a | — | — | — | — | — | — | — | — | — | — | L | | |
| | | b | — | — | — | — | — | — | — | — | — | — | L | | |
| | c + f | c | — | — | — | — | — | — | — | — | — | — | L | | |
| | | d | — | — | — | — | — | — | L | | | | | | |
| KP 5 | Flat | a | — | — | — | — | — | — | — | — | — | — | L | | |
| | | b | — | — | — | — | — | — | — | — | — | — | — | L | |
| | c + f | c | — | — | — | — | — | — | — | — | — | — | L | | |
| | | d | — | — | — | — | — | — | L | | | | | | |
| KP 6 | Flat | a | — | — | — | — | — | — | — | — | — | — | — | L | |
| | | b | — | — | — | — | — | — | — | — | — | — | L | | |
| | c + f | c | — | — | — | — | — | — | — | — | — | — | L | | |
| | | d | — | — | — | — | — | — | — | — | — | — | — | | L |

L = Break-through time period = visually noticeable fat spot/spots on the TLC plate placed under the material, actual penetration of the fat through the material.
c + f = Sample has been creased and folded before testing In view of the above detailed description of the present invention, other modifications and variations will become apparent to those skilled in the art. However, it should be apparent that such other modifications and variations may be effected without departing from the spirit and scope of the invention.

The invention claimed is:

1. A method for manufacturing a film wherein the method comprises the steps of:
   providing a suspension comprising a microfibrillated cellulose,
   adding an enzyme to the suspension,
   mixing the enzyme with the suspension to form a mixture,
   applying said mixture to a moving wire to form a fibrous web,
   dewatering the fibrous web on the moving wire at a production speed between 150-1500 m/min, and
   drying said web to form said film,
   wherein said film has a basis weight of less than 100 g/m$^2$ and an oxygen transmission rate in the range of from 0.1 to 300 cc/m$^2$/24 h according to ASTM D-3985, at a relative humidity of 50% at 23° C., at a relative humidity of 85% at 38° C., or at both.

2. The method according to claim 1 wherein the enzyme is an enzyme decomposing cellulose, hemicellulose, or both.

3. The method according to claim 1 wherein the enzyme is cellulase with an activity of more than 20 000 CMU/g, xylanase with an activity of more than 20 000 nkat/ml, or both.

4. The method according to claim 1 wherein the microfibrillated cellulose is native.

5. The method according to claim 1 wherein the temperature of the suspension when the enzyme is added is between 30-70° C.

6. The method according to claim 1 wherein mixture is stored for a period of at least 5 minutes before being applied to said wire.

7. The method according to claim 1 wherein a solid content of the mixture on a dry basis is between 0.01-0.5% by weight.

8. The method according to claim 1 wherein the method further comprises the step of mechanical treating the suspension comprising microfibrillated cellulose prior to the addition of the enzyme.

9. The method according to claim 1 wherein a solid content of the fibrous web on a dry basis before drying is between 20-50% by weight.

10. The method according to claim 1, wherein the drying is done at a temperature between 100-150° C.

11. The method according to claim 1, wherein said mixture consists essentially of the microfibrillated cellulose, the enzyme, and an additive selected from any one of a starch, carboxymethyl cellulose, a filler, retention chemicals, flocculation additives, deflocculating additives, dry strength additives, wet strength additives, softeners, surface active agents or mixtures thereof.

12. The method according to claim 1 wherein the suspension comprises more than 50 wt-% of microfibrillated cellulose by total amount of organic material in the suspension.

13. A method for manufacturing a film wherein the method comprises the steps of:
providing a suspension comprising a microfibrillated cellulose,
adding an enzyme to the suspension,
mixing the enzyme with the suspension to form a mixture consisting essentially of the microfibrillated cellulose, the enzyme, and an additive selected from any one of a starch, carboxymethyl cellulose, a filler, retention chemicals, flocculation additives, deflocculating additives, dry strength additives, wet strength additives, softeners, surface active agents or mixtures thereof, wherein a temperature of the suspension when the enzyme is added is between 30 and 70° C. and a pH of the suspension is between 4 and 8,
applying said mixture to a moving wire to form a fibrous web,
dewatering the fibrous web on the moving wire at a production speed between 150-1500 m/min, and
drying said web to form said film,
wherein said film has a basis weight of less than 100 g/m$^2$ and an oxygen transmission rate in the range of from 0.1 to 300 cc/m$^2$/24 h according to ASTM D-3985, at a relative humidity of 50% at 23° C., at a relative humidity of 85% at 38° C., or at both.

14. The method according to claim 13 wherein the enzyme is an enzyme decomposing cellulose, hemicellulose, or both.

15. The method according to claim 13 wherein the enzyme is cellulase with an activity of more than 20 000 CMU/g, xylanase with an activity of more than 20 000 nkat/ml, or both.

16. The method according to claim 13 wherein mixture is stored for a period of at least 5 minutes before being applied to said wire.

17. The method according to claim 13 wherein a solid content of the mixture on a dry basis is between 0.01-0.5% by weight; or wherein a solid content of the fibrous web on a dry basis before drying is between 20-50% by weight; or both.

18. The method according to claim 13 wherein the method further comprises the step of mechanical treating the suspension comprising microfibrillated cellulose prior to the addition of the enzyme.

19. The method according to claim 13, wherein the drying is done at a temperature between 100-150° C.

20. The method according to claim 13 wherein the suspension comprises more than 50 wt-% of microfibrillated cellulose by total amount of organic material in the suspension.

* * * * *